US009370785B2

(12) United States Patent
Ukigai et al.

(10) Patent No.: US 9,370,785 B2
(45) Date of Patent: Jun. 21, 2016

(54) SHOWER APPARATUS

(71) Applicant: TOTO LTD., Fukuoka (JP)

(72) Inventors: Kiyotake Ukigai, Kitakyushu (JP); Minoru Sato, Kitakyushu (JP); Takahiro Ohashi, Kitakyushu (JP); Yutaka Aihara, Kitakyushu (JP); Minami Okamoto, Kitakyushu (JP); Katsuya Nagata, Kitakyushu (JP)

(73) Assignee: TOTO LTD., Fukuoka (JP)

( * ) Notice: Subject to any disclaimer, the term of this patent is extended or adjusted under 35 U.S.C. 154(b) by 60 days.

(21) Appl. No.: 14/568,050

(22) Filed: Dec. 11, 2014

(65) Prior Publication Data

US 2015/0108255 A1 Apr. 23, 2015

Related U.S. Application Data

(63) Continuation of application No. 13/030,775, filed on Feb. 18, 2011, now Pat. No. 9,108,207.

(30) Foreign Application Priority Data

Feb. 18, 2010 (JP) ................................ 2010-033980

(51) Int. Cl.
*A61M 11/02* (2006.01)
*B05B 1/18* (2006.01)
*B05B 7/04* (2006.01)

(52) U.S. Cl.
CPC ............... *B05B 1/185* (2013.01); *B05B 7/0425* (2013.01)

(58) Field of Classification Search
CPC ........ B05B 7/0425; B05B 1/185; B05B 1/18; B05B 11/06; B05B 11/068; B05B 7/2408; E03C 2001/082; E03C 1/08; A61M 11/02; A61M 11/04
USPC .......... 239/10, 103, 419.5, 335, 425.5, 428.5, 239/426, 434, 366, 368, 369, 553.3, 553.5
See application file for complete search history.

(56) References Cited

U.S. PATENT DOCUMENTS 2,707,624 A * 5/1955 Shames .................. E03C 1/084 210/460
2,741,467 A 4/1956 Lee et al.

(Continued)

FOREIGN PATENT DOCUMENTS

EP 2260945 A1 12/2010
GB 2470805 A 12/2010

(Continued)

OTHER PUBLICATIONS

The Extended European Search Report dated Jun. 1, 2011; Application No. 11250196.0-2425.

*Primary Examiner* — Arthur O Hall
*Assistant Examiner* — Chee-Chong Lee
(74) *Attorney, Agent, or Firm* — Studebaker & Brackett PC

(57) ABSTRACT

Provided is a shower apparatus which can stably supply bubbly water through all nozzle holes and can cause water droplets of large, uniform size to land continuously on the user so as to allow the user to enjoy a shower with a voluminous feel as if the user were being showered by large drops of rain. The shower apparatus includes a water supply unit, a throttle unit adapted to eject passing water downstream, an aeration unit adapted to produce bubbly water by aerating the water ejected through the throttle unit, and a nozzle unit provided with a plurality of nozzle holes used to discharge the bubbly water, wherein the throttle unit has a flat-shaped throttle channel and water ejected through the throttle channel plunges into an air-liquid interface as a sheet-like stream, thereby producing bubbly water, which is then discharged through the nozzle hole.

2 Claims, 16 Drawing Sheets

(56) References Cited

U.S. PATENT DOCUMENTS

| | | | | |
|---|---|---|---|---|
| 3,330,486 | A * | 7/1967 | Semple | B01F 3/0473 239/17 |
| 3,358,934 | A | 12/1967 | Moen | |
| 3,524,591 | A | 8/1970 | Samuels et al. | |
| 4,346,844 | A * | 8/1982 | Harmony | B05B 1/1636 239/428.5 |
| 4,637,552 | A * | 1/1987 | Finkbeiner | E03C 1/084 239/428.5 |
| 5,111,994 | A | 5/1992 | Gonzalez | |
| 7,913,934 | B2 | 3/2011 | Schorn | |
| 2006/0151640 | A1 * | 7/2006 | Miura | B05B 1/14 239/589 |
| 2006/0163391 | A1 | 7/2006 | Schorn | |
| 2008/0011880 | A1 * | 1/2008 | Butzke | B05B 1/185 239/428.5 |
| 2008/0272212 | A1 | 11/2008 | Denzler | |
| 2009/0266430 | A1 | 10/2009 | Yang | |

FOREIGN PATENT DOCUMENTS

| | | | |
|---|---|---|---|
| JP | 06-182262 | A | 7/1994 |
| JP | 2002-102100 | A | 4/2002 |
| JP | 3747323 | B1 | 2/2006 |
| JP | 2006-509629 | A | 3/2006 |
| JP | 2006-239106 | A | 9/2006 |
| JP | 2009-279484 | A | 12/2009 |
| JP | 2010-162532 | A | 7/2010 |
| JP | 2010-188046 | A | 9/2010 |
| WO | 81/02253 | A1 | 8/1981 |
| WO | 2004/052550 | A1 | 6/2004 |
| WO | 2010/070904 | A1 | 6/2010 |

* cited by examiner

SHOWER APPARATUS

BACKGROUND OF THE INVENTION

1. Field of the Invention

The present invention relates to a shower apparatus.

2. Description of the Related Art

In the present technical field, a shower apparatus is known which discharges bubbly water by aerating water using a so-called ejector effect. Since the water flowing into the shower apparatus is distributed to multiple nozzle holes and sprayed therefrom, when the spray is aerated, the water flowing into the apparatus is aerated before being distributed among the nozzle holes.

An example of such a shower apparatus is proposed in National Publication of International Patent Application No. 2006-509629. The shower apparatus described in National Publication of International Patent Application No. 2006-509629 comprises a plurality of nozzle holes provided in a front face of a disk-shaped housing shell and is configured to discharge water flowing in through the center of a rear face of the housing shell by distributing the water to the plurality of nozzle holes. The shower apparatus produces bubbly water by aerating the water which has flowed into the housing shell and distributes the bubbly water to the plurality of nozzle holes formed so as to distribute over the entire front face of the housing shell. Therefore, a turbulence generation/expansion unit is placed in a traveling direction of the bubbly water, causing the bubbly water to change direction by colliding with the turbulence generation/expansion unit and thereby spread over the entire front face of the housing shell.

Another example of a shower apparatus is proposed in Japanese Patent Laid-Open No. 2006-239106. With the shower apparatus described in Japanese Patent Laid-Open No. 2006-239106, when a cock such as a hot and cold mixer tap is opened, water is supplied from a hose and passed through an orifice member. Then, the water is mixed with air sucked through an inner suction port open to a decompression chamber installed on a downstream side of the orifice member and maintained under reduced pressure at the given moment. The shower apparatus described in Japanese Patent Laid-Open No. 2006-239106 produces bubbly water in this way and discharges the bubbly water through a plurality of nozzle holes provided in a shower head. With the shower apparatus, the produced bubbly water proceeds to the nozzle holes by changing direction by hitting a threaded member in a partitioned pipe installed on the downstream side of the decompression chamber as well as inner walls of the shower head installed further downstream.

SUMMARY OF THE INVENTION

In spraying a shower using bubbly water produced by aerating water, how to set the feel of the bubbly water hitting a user plays an important role in a quality feel experienced by the user who takes a shower. The shower apparatus described in Japanese Patent Laid-Open No. 2006-239106 is intended to achieve the sensation of water hitting the user intermittently as described in paragraph 0015 of the patent literature. The term "intermittently" means that finely divided water droplets of nonuniform sizes hit the user. It is considered that the term expresses a mixed sensation of strong and weak showers which can be experienced by the user if hit by large-size water droplets which produce a sensation of a strong shower and small-size water droplets which produce a sensation of a weak shower. According to concrete studies conducted by the present inventors, it is presumed that in the bubbly water just produced, water is mixed substantially uniformly with air. Subsequently, the bubbles collide with each other as the produced bubbly water changes direction by hitting the threaded member and the inner walls of the shower head, and it is considered that bubble diameters are nonuniform when the bubbly water reaches the nozzle holes. Then, when discharged from the nozzle holes, the bubbly water turns into water droplets of nonuniform sizes. It is considered that the sensation described above is achieved by directing the water droplets of nonuniform sizes at the user.

On the other hand, National Publication of International Patent Application No. 2006-509629 does not give any concrete description of properties of the bubbly water discharged from the shower apparatus described in the patent literature. However, as in the case of the shower apparatus described in Japanese Patent Laid-Open No. 2006-239106, it is considered that the shower apparatus described in National Publication of International Patent Application No. 2006-509629 produces water droplets of nonuniform sizes by supplying and discharging bubbly water with nonuniform bubble diameters from the nozzle holes and directs the water droplets of nonuniform sizes at the user. In the shower apparatus described in National Publication of International Patent Application No. 2006-509629, the turbulence generation/expansion unit is placed in the traveling direction of the bubbly water, causing the bubbly water to change direction by colliding with the turbulence generation/expansion unit. Thus, presumably similar nonuniform bubble growth takes place in the shower apparatus described in J National Publication of International Patent Application No. 2006-509629 and resulting water droplets of nonuniform sizes are directed at the user.

Under these circumstances, the present inventors intended to provide a shower apparatus which enables spray of a shower with a comfortable voluminous feel as if one were being showered by large drops of rain. The above-described conventional techniques, which achieve the sensation of nonuniformly-sized water droplets hitting the user as described above, do not provide spray of a shower with a voluminous feel as if the user were being showered by large drops of rain.

To provide spray of a shower with such a new feel, the present inventors paid attention to the state of bubbly water in nozzle holes and just after discharge from the nozzle holes. In the nozzle holes and after discharge from the nozzle holes, since the bubbly water is in a state of gas-liquid, two-phase flow in which two different types of fluid—gas and liquid—coexist and move in the same flow conduit, the bubbly water is considered to be flowing in any of the typical flow patterns of bubble flow, slug flow, and annular flow. Since these flow patterns differ in the manner of bubble inclusion, it is considered that they also differ in the manner of fine division after discharge from the nozzle holes. Thus, the present inventors assumed that with the conventional techniques, since the bubble diameters in the bubbly water supplied to the nozzle holes are nonuniform, the bubbly water is discharged under the coexistence of bubble flow, slug flow, and annular flow, resulting in the sensation of nonuniformly-sized water droplets hitting the user. Based on this assumption, the present inventors considered it important to control the bubble diameters of the bubbly water supplied to the nozzle holes to be uniform.

However, since water is normally supplied to a shower apparatus through a single supply port, bubbly water is produced by aerating the water supplied through the single supply port. On the other hand, since multiple nozzle holes are provided, the bubbly water is stimulated when being distributed to the nozzle holes by changing the direction of the bubbly water, and thus it is extremely difficult to discharge the water from the nozzle holes without causing the air bubbles to grow.

To solve this problem, the present inventors worked out a basic concept of a shower apparatus which causes finely divided water droplets of relatively large, uniform size to land continuously on the user by supplying bubbly water whose bubble diameter is kept as uniform as possible to the nozzle holes. Such a shower apparatus allows the user to enjoy a shower with a voluminous feel as if the user were being showered by large drops of rain.

The shower apparatus thus conceived by the present inventors causes finely divided water droplets of relatively large, uniform size to land continuously on the user by supplying bubbly water whose bubble diameter is kept as uniform as possible to the nozzle holes and thereby allows the user to enjoy a shower with a voluminous feel as if the user were being showered by large drops of rain. Specifically, the shower apparatus includes a water supply unit adapted to supply water, a throttle unit installed downstream of the water supply unit and adapted to make a cross sectional area of a flow channel smaller than the water supply unit and thereby eject passing water downstream, an aeration unit installed downstream of the throttle unit and provided with an opening adapted to produce bubbly water by aerating the water ejected through the throttle unit, and a nozzle unit installed downstream of the aeration unit and provided with a plurality of nozzle holes adapted to discharge the bubbly water.

This configuration does provide a shower which offers a voluminous feel as if one were being showered by large drops of rain, such as described above. However, for example, if the face of the nozzle unit in which the nozzle holes are formed is increased in area, the bubbles may rise and stagnate due to buoyancy in regions distant from the throttle unit depending on circumstances. The present inventors found a new problem not encountered conventionally: namely, if bubbles rise and stagnate due to buoyancy in this way, bubbly water is not supplied stably to the nozzle holes.

The present invention has been made in view of the above problem and has an object to provide a shower apparatus which can stably supply bubbly water through all nozzle holes as well as can supply bubbly water to the nozzle holes by keeping the bubble diameter in the bubbly water as uniform as possible, and thereby cause water droplets of relatively large, uniform size to land continuously on the user so as to allow the user to enjoy a shower with a voluminous feel as if the user were being showered by large drops of rain.

To solve the above problem, the present invention provides a shower apparatus for discharging aerated bubbly water, comprising: a water supply unit adapted to supply water; a throttle unit installed downstream of the water supply unit and adapted to make a cross sectional area of a flow channel smaller than the water supply unit and thereby eject passing water downstream; an aeration unit installed downstream of the throttle unit and provided with an opening adapted to produce the bubbly water by aerating the water ejected through the throttle unit; and a nozzle unit installed downstream of the aeration unit and provided with a plurality of nozzle holes adapted to discharge the bubbly water by being formed along an ejection direction of the water ejected through the throttle unit. The throttle unit comprises at least one throttle channel formed into a flat shape whose longer sides run along a nozzle face in which the plurality of nozzle holes are provided. The water ejected from the throttle channel becomes a sheet-like stream of water, which plunges into an air-liquid interface by involving air taken in through the opening and thereby producing bubbly water, where the air-liquid interface is an interface between air and water, the water having been temporarily pooled in the aeration unit and the nozzle unit. The produced bubbly water is discharged through the nozzle hole.

According to the present invention, the water supplied from the water supply unit is ejected to the aeration unit and nozzle unit through the throttle unit, and the water temporarily pooled in the aeration unit and nozzle unit is discharged outside through the plurality of nozzle holes in the nozzle unit. By involving air taken in through the opening formed in the aeration unit, the water ejected through the throttle unit plunges into an air-liquid interface between air and the water temporarily pooled in the aeration unit and nozzle unit and thereby turns into bubbly water to be sprayed through the plurality of nozzle holes in the nozzle unit.

In a stage in which the water ejected through the throttle unit plunges into the air-liquid interface and thereby turns into bubbly water, the air bubbles in the bubbly water can be configured to have a substantially uniform diameter. Thus, the bubbly water can reach the location where the nozzle holes are formed while maintaining the substantially uniform diameter. As the bubbly water containing air bubbles of such a substantially uniform diameter is supplied to the nozzle holes, a bubble flow or slug flow can be formed in the nozzle holes or just after discharge from the nozzle holes. When discharged from the nozzle holes, the bubbly water containing air bubbles of such a substantially uniform diameter and formed as a bubble flow or slug flow in this way is finely divided substantially uniformly by being sheared in a direction substantially orthogonal to a discharge direction without being turned into a mist as in the case of an annular flow. This causes finely divided water droplets of relatively large, uniform size to land continuously on the user and thereby allows the user to enjoy a shower with a voluminous feel as if the user were being showered by large drops of rain.

Furthermore, according to the present invention, to produce bubbly water containing finer bubbles, the throttle channel of the throttle unit is formed into a flat shape whose longer sides run along a nozzle face in which the plurality of nozzle holes are provided. The water stream ejected from the throttle channel of the flat shape rushes toward the air-liquid interface as a sheet-like stream of water having a flat cross-sectional shape. When the sheet-like stream of water plunges into the air-liquid interface, in a region along the sheet-like stream of water, convection currents arranged along the direction in which the sheet-like stream of water plunges into the air-liquid interface are generated along a direction in which the sheet-like stream of water extends in a substantially planar fashion. When such convection currents are generated, generating directions of the convection currents coincide with each other on one side of the sheet-like stream of water and the rotational direction of the convection currents are opposite to the rotational direction of convection currents generated on the other side, but the traveling directions of the convection currents coincide with each other near the air-liquid interface into which the sheet-like stream of water plunges, reducing fears that neighboring convection currents will collide with each other. On opposite ends of the sheet-like stream of water, in addition to the convection currents described above, convection currents toward the opposite ends of the sheet-like stream of water are also generated, but in regions other than the opposite ends of the sheet-like stream of water, only convection currents moving toward the sheet-like stream of water from opposite sides are generated, also reducing collisions of convection currents near the air-liquid interface when viewed as a whole.

On the other hand, when a linear stream of water is caused to plunge into the air-liquid interface, since the water stream plunges into the air-liquid interface as a point rather than a line, convection currents are generated from all directions around the entry point centering on the linear stream of water. In this way, when convection currents toward the entry point of the plunging linear stream of water are generated from all directions around the entry point, the convection currents are put on collision course with each other. Therefore, when a linear stream of water is caused to plunge into the air-liquid interface, the convection currents generated around the entry point of the linear stream of water tend to collide with each other. This will cause collisions of air bubbles, which may result in enlargement of the air bubbles.

On the other hand, when a sheet-like stream of water is generated as in the case of the present invention, convection currents which are less prone to collisions with each other are generated on both sides of an entry line along which the sheet-like stream of water plunges, as described above. Convection currents less prone to collisions with each other, when generated in this way, can reduce the possibility of air bubble enlargement due to collisions of air bubbles. If the air bubbles in the bubbly water are broken up into minute bubbles and the flow of bubbly water is made less prone to collisions, thereby maintaining the minute bubbles, even if the nozzle holes are placed at locations distant from the throttle channel, the air bubbles are supplied to the nozzle holes without being affected by buoyancy. This makes it possible to supply the bubbly water stably through all the nozzle holes.

Also, in the shower apparatus according to the present invention, preferably the air-liquid interface is formed downstream of the opening, but upstream of the nozzle holes.

According to this preferred aspect, the water ejected from the throttle channel plunges into the air-liquid interface as a sheet-like stream of water. This allows forces applied by the ejected water to be transmitted uniformly to the entire air-liquid interface, making it possible to stably position the air-liquid interface between the nozzle holes and opening. In this way, since the air-liquid interface is formed stably and the bubbly water is produced by causing the sheet-like stream of water ejected from the throttle channel to plunge into the air-liquid interface, it is possible to induce such a flow of water that will involve surrounding air at the stable air-liquid interface as well as to increase the number of air bubbles without enlarging the air bubbles also because the convection currents around the water stream plunging into the air-liquid interface are less prone to collisions with each other.

Also, in the shower apparatus according to the present invention, preferably at least a pair of the openings are provided, being placed on opposite sides of the sheet-like stream of water.

According to the present invention, the ejection of the sheet-like stream of water from the throttle channel has the effect of inhibiting enlargement of the air bubbles as described above, but the movement of air across the water stream is restricted. However, according to this preferred aspect, since the openings are provided on opposite sides of the sheet-like stream of water, air can be supplied evenly to both sides of the sheet-like stream, contributing to smooth production of the bubbly water.

Also, in the shower apparatus according to the present invention, preferably a plurality of the throttle channels are installed side by side in a direction along the nozzle face. Also, preferably the plurality of throttle channels installed side by side are arranged by keeping a predetermined spacing from each other such that air can pass among sheet-like streams of water ejected from the respective throttle channels.

According to the present invention, the ejection of the sheet-like stream of water from the throttle channel has the effect of inhibiting enlargement of the air bubbles as described above, but the movement of air across the water stream is restricted. However, according to this preferred aspect, since a plurality of the flat-shaped throttle channels are installed side by side by keeping a predetermined spacing from each other, gaps are formed among the sheet-like stream of water, allowing air to pass therethrough. Therefore, air can travel between opposite sides of the sheet-like streams, and thus air can be supplied evenly to both sides of the sheet-like streams, contributing to smooth production of the bubbly water.

Also, in the shower apparatus according to the present invention, preferably the opening is provided only on one side of the sheet-like streams of water.

According to this preferred aspect, since air can travel between opposite sides of the sheet-like streams, even if the opening is provided only on one side of the sheet-like streams, air can be supplied evenly to both sides of the sheet-like streams. Thus, the simple structure in which the opening is provided only on one side of the sheet-like streams can contribute to smooth production of the bubbly water.

Also, in the shower apparatus according to the present invention, preferably the throttle channel is configured to radially eject the sheet-like stream of water; and the plurality of nozzle holes are arranged by being scattered in a region in which the sheet-like stream of water is ejected.

According to this preferred aspect, since the sheet-like stream of water is ejected radially from the throttle channel, the sheet-like stream of water can be ejected so as to spread out from the throttle channel, allowing the sheet-like stream of water to reach to a wider region. Furthermore, since the sheet-like stream of water is ejected so as to spread out from the throttle channel, the sheet-like stream of water is ejected, spreading out thinly, plunging into the air-liquid interface as a thinner sheet-like stream of water, and thereby making it possible to produce bubbly water containing finer bubbles. In this way, since the plurality of nozzle holes are arranged by being scattered in the region in which the sheet-like stream of water is ejected, the plurality of nozzle holes can be placed in a wider region and bubbly water containing finer bubbles can be supplied to the plurality of nozzle holes.

Also, in the shower apparatus according to the present invention, preferably the sheet-like stream of water is ejected radially from the throttle channel by being separated into fan-shaped portions.

According to this preferred aspect, since the sheet-like stream of water is ejected radially from the throttle channel by being separated into fan-shaped portions, gaps are created, allowing air to pass therethrough. Therefore, air can travel between opposite sides of the sheet-like streams, and air can be supplied evenly to both sides of the sheet-like streams, contributing to smooth production of the bubbly water.

The present invention provides a shower apparatus which can stably discharge bubbly water through all nozzle holes as well as can supply bubbly water to the nozzle holes by keeping bubble diameter in the bubbly water as uniform as possible, and thereby cause water droplets of relatively large, uniform size to land continuously on the user so as to allow the user to enjoy a shower with a voluminous feel as if the user were being showered by large drops of rain.

BRIEF DESCRIPTION OF THE DRAWINGS

FIG. 1(A) is a plan view, FIG. 1(B) is a side view, and FIG. 1(C) is a bottom view;

FIG. 8(A) is a plan view, FIG. 8(B) is a side view, and FIG. 8(C) is a bottom view;

DESCRIPTION OF SYMBOLS

Figure 1A:
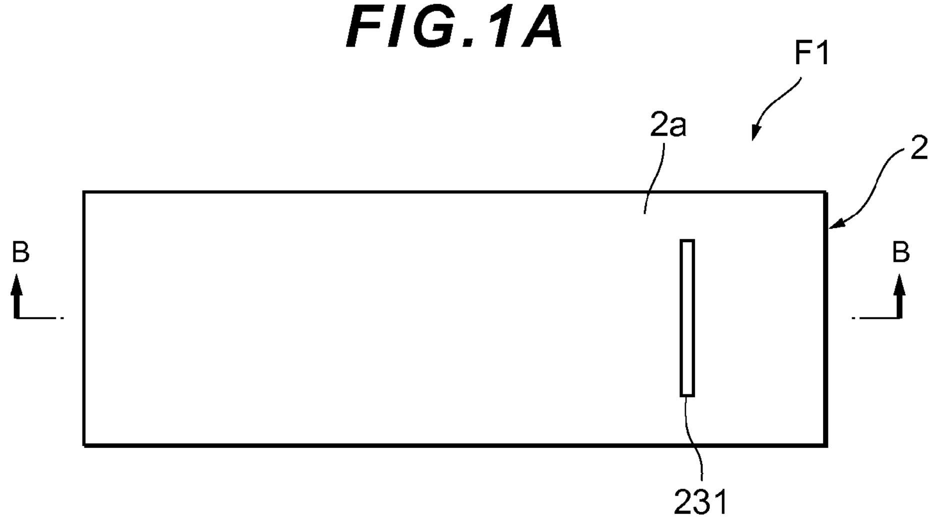
FIGS. 1(A) to 1(C) are diagrams showing a shower apparatus according to a first embodiment of the present invention, where

F1: Shower apparatus
2: Body
2*a*: Top face
2*b*: Bottom face
21: Water supply unit
21*a*: Front wall surface
21*b*: Side wall
21*c*: Side wall
21*d*: Water supply port
21*e*: Side wall
21*f*: Side wall
22: Throttle unit
22*a*: Partition wall
22*b*: Side wall
22*c*: Side wall
22*e*: Side wall
22*f*: Side wall
221: Throttle channel
23: Aeration unit
23*b*: Side wall
23*c*: Side wall
23*d*: Side wall
23*ea*: Side wall
23*eb*: Side wall
23*fa*: Side wall
23*fb*: Side wall
23*g*: Stepped portion
231: Opening
24: Nozzle unit
24*a*: Side wall
24*b*: Side wall
24*c*: Side wall
24*e*: Side wall
24*f*: Side wall
242: Nozzle stub
243: Nozzle holes
BW: Bubbly water
BW1: Virtual water ejection straight line
BW2: Water stream
BW3: Air-liquid interface
WF: Sheet-like stream
WFs: Linear stream
F3: Shower apparatus
4: Body
4A: Cavity
4Aa: Abutting face
4Ab: Concave portion
4Ac: Through-hole
4B: Shower plate
4Ba: Abutting face
4Bb: Through-hole
4Bc: Concave portion
4C: Water ejection piece
4Ca: Air introducing projection
4Cb: Flange
4Cd: Throttle projection
4*a*: Top face
4*b*: Bottom face
41: Water supply unit
41*d*: Water supply port
42: Throttle unit
421: Throttle channel
43: Aeration unit
43*b*: Side wall
43*c*: Side wall
431: Opening
431*a*: Air introduction hole
44: Nozzle unit
44*a*: Side wall
44*b*: Side wall
44*c*: Side wall
443: Nozzle hole

DETAILED DESCRIPTION OF THE PREFERRED EMBODIMENTS

An embodiment of the present invention will be described below with reference to the accompanying drawings. To facilitate understanding of the description, the same components in different drawings are denoted by the same reference numerals whenever possible and redundant description thereof will be omitted.

Figure 1B:
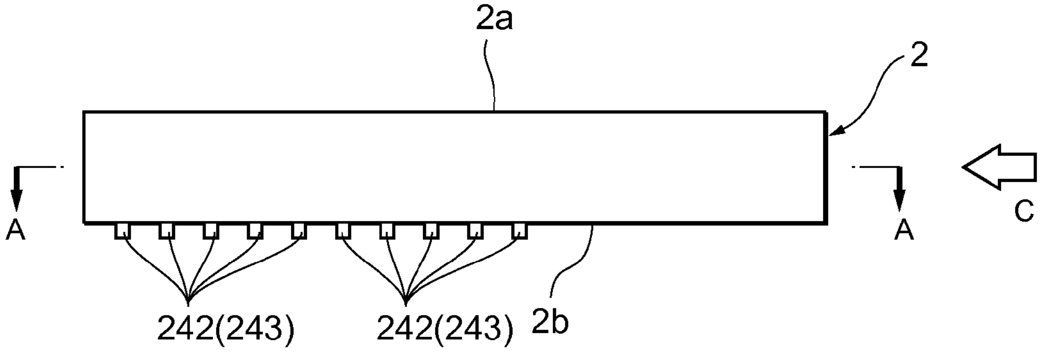
Figure 1C:
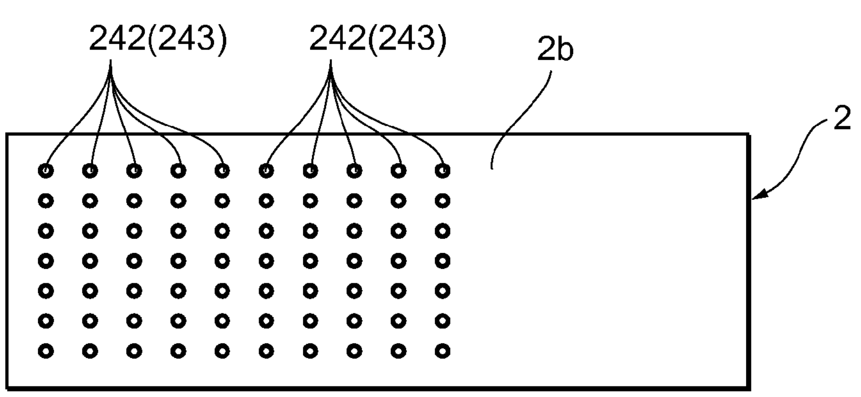

Next, a shower apparatus which is a first embodiment of the present invention will be described with reference to FIGS. 1(A) to 1(C). FIGS. 1(A) to 1(C) are diagrams showing a shower apparatus F1 according to a first embodiment of the present invention, where FIG. 1(A) is a plan view, FIG. 1(B) is a side view, and FIG. 1(C) is a bottom view.

As shown in FIG. 1(A), the shower apparatus F1 mainly includes a body 2 shaped substantially as a rectangular parallelepiped, and an opening 231 is formed in a top face 2*a* of the shower apparatus F1 (body 2). As shown in FIG. 1(B), a plurality of nozzle stubs 242 are provided in a bottom face 2*b* opposite the top face 2*a* of the shower apparatus F1. A nozzle hole 243 is formed in each nozzle stub 242. As shown in FIG. 1(C), the plurality of nozzle stubs 242 are provided in the bottom face 2*b* of the body 2. According to the present embodiment, seven rows by ten columns of nozzle stubs 242 are formed for a total of 70 nozzle stubs.

Figure 2:
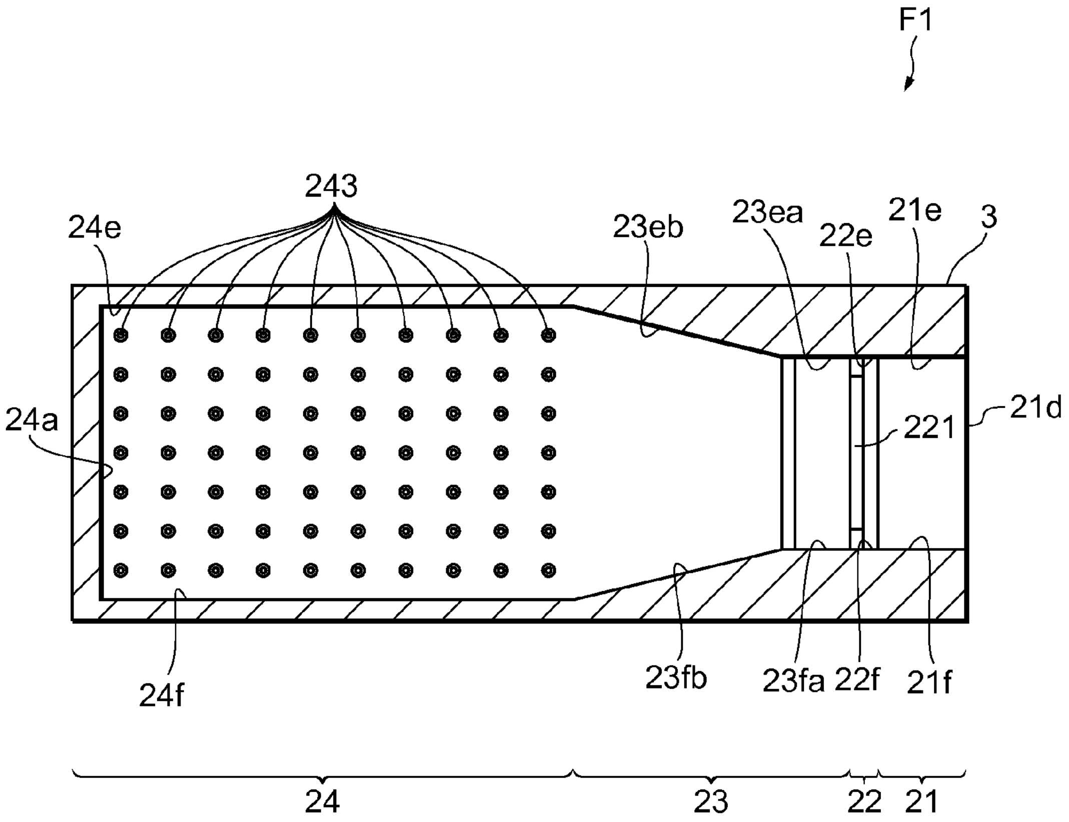
FIG. 2 is a sectional view taken along line A-A in FIG. 1(B)

Next, the shower apparatus F1 will be described with reference to FIG. 2, which is a sectional view taken along line C-C in FIG. 1(B). As shown in FIG. 2, the shower apparatus F1 includes a water supply unit 21, throttle unit 22, aeration unit 23, and nozzle unit 24.

The water supply unit 21 is a part intended to supply water and adapted to supply water introduced through a water supply port 21*d* to the throttle unit 22. The water supply port 21*d* can be connected with water supply means (such as a water supply hose: not shown) and the water supplied through the water supply means is supplied from the water supply unit 21 to the throttle unit 22. The water supply unit 21 includes a side wall 21*e* and a side wall 21*f* running along the traveling direction of water as part of the body 2 by being placed so as to be parallel to each other.

The throttle unit 22 is a part installed downstream of the water supply unit 21 and adapted to make the cross sectional area of a flow channel smaller than the water supply unit 21 and thereby eject passing water downstream. The throttle unit 22 includes a side wall 22*e* and side wall 22*f* running along the traveling direction of water as part of the body 2 by being placed so as to be parallel to each other.

A single throttle channel 221 is installed in the throttle unit 22. The throttle channel 221 is formed into a flat, slit-like shape whose longer sides run along the direction from the side wall 22*e* to the side wall 22*f*.

Figure 4:
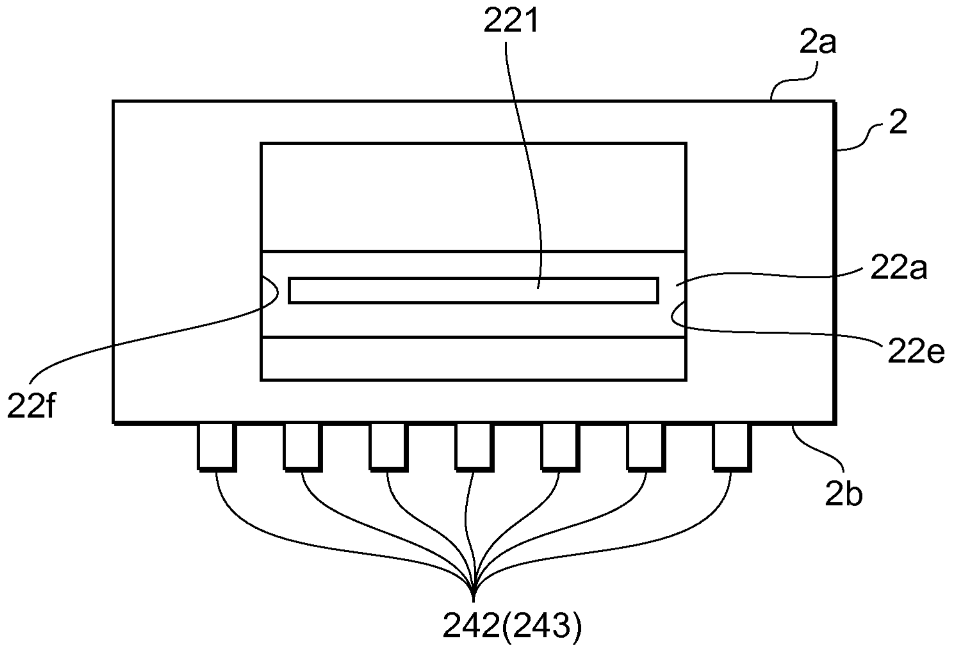
FIG. 4 is a view taken in the direction of arrow C in FIG. 1(B)

FIG. 4 shows what the throttle channel 221 looks like. FIG. 4 is a view taken in the direction of arrow C in FIG. 1(B). As shown in FIG. 4, the throttle channel 221 is formed into a flat, slit-like shape whose longer sides run along the top face 2*a* and bottom face 2*b* of the body 2 and whose shorter sides run along the side wall 22*e* and side wall 22*f*.

Returning to FIG. 2, description of other parts will be continued. The aeration unit 23 is a part installed downstream of the throttle unit 22 and provided with the opening 231 used to aerate the water ejected through the throttle unit 22 and thereby turn the water into bubbly water. The aeration unit 23 includes side walls 23*ea* and 23*eb* and side walls 23*fa* and 23*fb*, as part of the body 2, along a traveling direction of water.

The side wall 23*ea* and side wall 23*fa* are placed so as to be parallel to each other. The side wall 23*eb* is installed downstream of the side wall 23*ea* consecutively with the side wall 23*ea* and placed obliquely so as to expand the flow channel outward from a portion connected to the side wall 23*ea* downstream. Similarly, the side wall 23*fb* is installed downstream of the side wall 23*fa* consecutively with the side wall 23*fa* and placed obliquely so as to expand the flow channel outward from a portion connected to the side wall 23*fa* downstream.

The nozzle unit 24 is a part installed downstream of the aeration unit 23 and provided with the plurality of nozzle holes 243 used to discharge bubbly water. The nozzle holes 243 are formed in the nozzle stubs 242 (not illustrated specifically in FIG. 2).

As shown in FIG. 2, the side wall 21*e* of the water supply unit 21, the side wall 22*e* of the throttle unit 22, and the side wall 23*ea* which makes up part of the aeration unit 23 are placed so as to lie in the same plane. Another side wall of the aeration unit 23, i.e., the side wall 23*eb*, is placed obliquely, being oriented towards outer side faces of the body 2, and is connected to a side wall 24*e* of the nozzle unit 24. Similarly, the side wall 21*f* of the water supply unit 21, the side wall 22*f* of the throttle unit 22, and the side wall 23*fa* which makes up part of the aeration unit 23 are placed so as to lie in the same plane. Another side wall of the aeration unit 23, i.e., the side wall 23*fb*, is placed obliquely, being oriented towards outer side faces of the body 2, and is connected to a side wall 24*f* of the nozzle unit 24.

Figure 3:
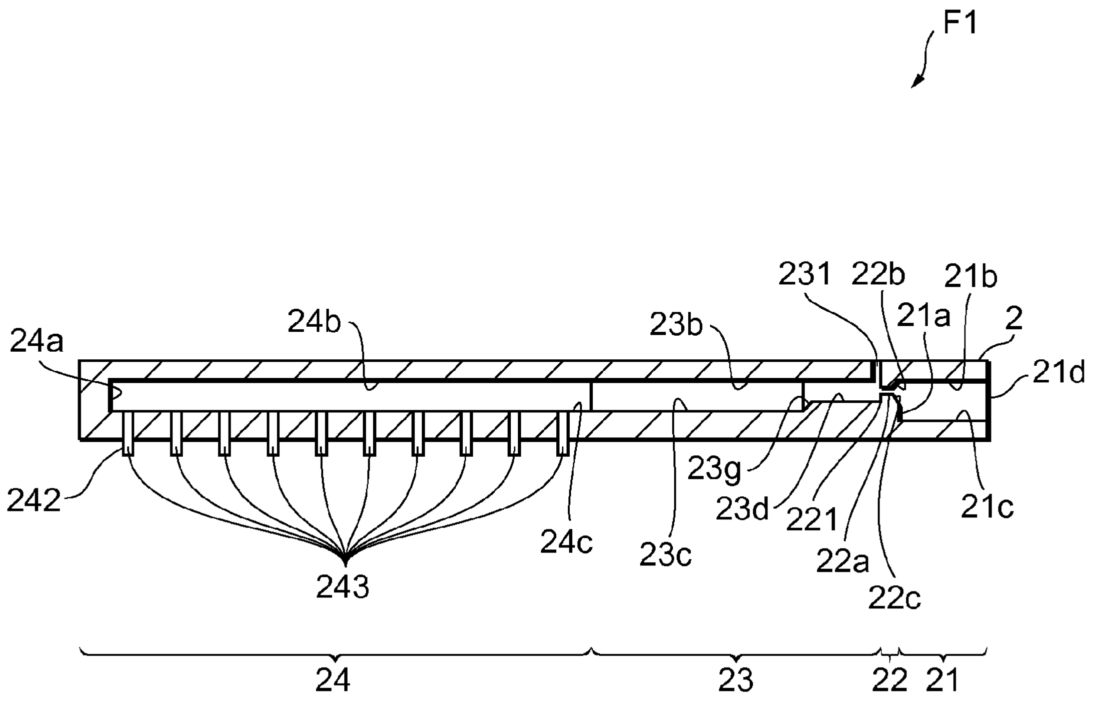
FIG. 3 is a sectional perspective view taken along line B-B in FIG. 1(A)

Next, the shower apparatus F1 will be described with reference to FIG. 3, which is a sectional view taken along line B-B in FIG. 1(A). As shown in FIG. 3, the water supply unit 21 has a side wall 21*b* and side wall 21*c* which connect the side wall 21*e* and side wall 21*f* with each other. The side wall 21*b* and side wall 21*c* are formed to be longer in length along a direction orthogonal to the direction in which water proceeds than the side wall 21*e* and side wall 21*f*. Thus, the water supply unit 21 is formed such that the cross section of the flow channel will have a flat shape. A front wall surface 21*a* is installed in a boundary portion between the water supply unit 21 and throttle unit 22, and the side walls 21*e*, 21*f*, 21*b*, and 21*c* are connected to the front wall surface 21*a*. The front wall surface 21*a* is made up of a portion which extends from the side wall 21*b* to the side wall 21*c* and a portion which extends from the side wall 21*c* to the side wall 21*b*.

The throttle unit 22 is installed in a region on the downstream side beyond the front wall surface 21*a*. The throttle unit 22 has a side wall 22*b* and side wall 22*c* which connect the side wall 22*e* and side wall 22*f* with each other. The side wall 22*b* and side wall 22*c* are formed to be longer in length along a direction orthogonal to the direction in which water proceeds than the side wall 22*e* and side wall 22*f*. Thus, the cross section of the flow channel surrounded by the side walls 22*b*, 22*c*, 22*e*, and 22*f* of the throttle unit 22 is formed to have a flat shape. A partition wall 22*a* is installed in a boundary portion between the throttle unit 22 and aeration unit 23, and the side walls 22*e*, 22*f*, 22*b*, and 22*c* are connected to the partition wall 22*a*. The throttle channel 221 of a flat, slit-like shape is formed in the partition wall 22*a*.

The aeration unit 23 is installed in a region on the downstream side beyond the partition wall 22*a*. The aeration unit 23 includes a side wall 23*b*, side wall 23*c*, and side wall 23*d* which connect the side walls 23*ea* and 23*eb* with the side walls 23*fa* and 23*fb*, where the side wall 23*c* is placed at a location opposite to and relatively distant from the side wall 23*b* and the side wall 23*d* is placed at a location opposite to and relatively close to the side wall 23*b*. The side wall 23*c* is placed on the side of the nozzle unit 24 and the side wall 23*d* is placed on the side of the throttle unit 22. Besides, a stepped portion 23*g* is formed to connect the side wall 23*c* with the side wall 23*d*. The side walls 23*b*, 23*c*, and 23*d* are formed to be longer in length along a direction orthogonal to the direction in which water proceeds than the side walls 23*ea* and 23*eb* and side walls 23*fa* and 23*fb*. Therefore, the aeration unit 23 is formed such that the cross section of the flow channel will have a flat shape.

The nozzle unit 24 is installed in a region downstream of the side wall 23*c*. The nozzle unit 24 includes a side wall 24*b* connecting the side wall 24*e* with the side wall 24*f* and lying in the same plane as the side wall 23*b* of the aeration unit 23. Furthermore, the nozzle unit 24 includes a side wall 24*c* connecting the side wall 24*e* with the side wall 24*f* and lying in the same plane as the side wall 23*c* of the aeration unit 23. The side walls 24*b*, 24*c*, 24*e*, and 24*f* are connected to an inner-side side wall 24*a* which faces the water supply port 21*d* and functions as a terminal end of the flow channel. The nozzle stubs 242 protruding from the bottom face 2*b* of the body 2 are formed in the nozzle unit 24 and the nozzle holes 243 are formed in the nozzle stubs 242.

Figure 5:
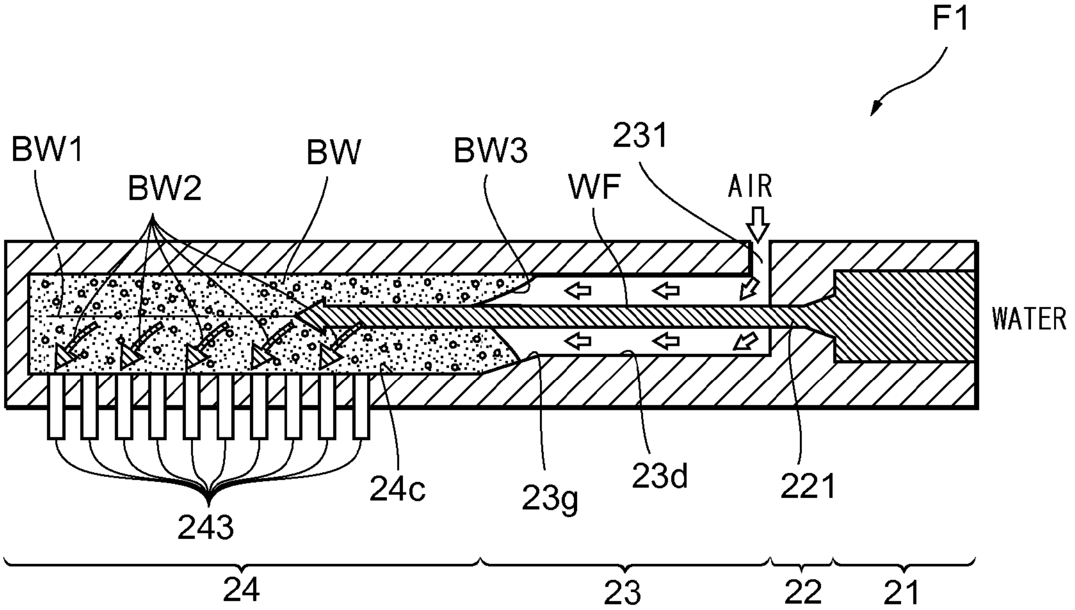
FIG. 5 is a sectional view taken along line B-B in FIG. 1(A), showing a flow of water in the shower apparatus.

Next, flow of water in the shower apparatus F1 will be described with reference to FIG. 5. FIG. 5 is a simplified sectional view taken along line B-B in FIG. 1(A), showing a state of water in the shower apparatus F1 being supplied with water.

As shown in FIG. 5, when water is supplied to the water supply unit 21 from water supply means (not shown) at or above a predetermined pressure, the water is ejected downstream through the throttle channel 221 formed in the throttle unit 22. A sheet-like stream WF, which is a sheet-like stream of water, is ejected downstream to the aeration unit 23 and the nozzle unit 24 from the throttle channels 221 such that a virtual water ejection straight line BW1 will extend to the most distant nozzle hole 243 while avoiding interference with the side walls 23*b*, 23*c*, 23*d*, 23*e*, and 23*f* of the aeration unit 23 and the side walls 24*b*, 24*c*, 24*d*, and 24*e* of the nozzle unit 24. The virtual water ejection straight line BW1 is a virtual straight line obtained by extending an ejection direction of the water ejected from the throttle unit 22.

When a sheet-like stream is ejected from the throttle unit 22 in this way, water is temporarily accumulated in at least part of the nozzle unit 24 and aeration unit 23, forming an air-liquid interface BW3, which is an interface between air and the accumulated water. Consequently, the water ejected along the virtual water ejection straight line BW1 plunges into the accumulated water through the air-liquid interface BW3 by involving the air existing in the aeration unit 23 and thereby produces bubbly water BW. The bubbly water BW is divided into water streams BW2 and discharged outside through the nozzle holes 243. Since the opening 231 is formed in the aeration unit 23, air can always be kept supplied even though the sheet-like stream ejected along the virtual water ejection straight line BW1 plunges into the accumulated water through the air-liquid interface BW3 by involving the air existing in the aeration unit 23.

Figure 6:
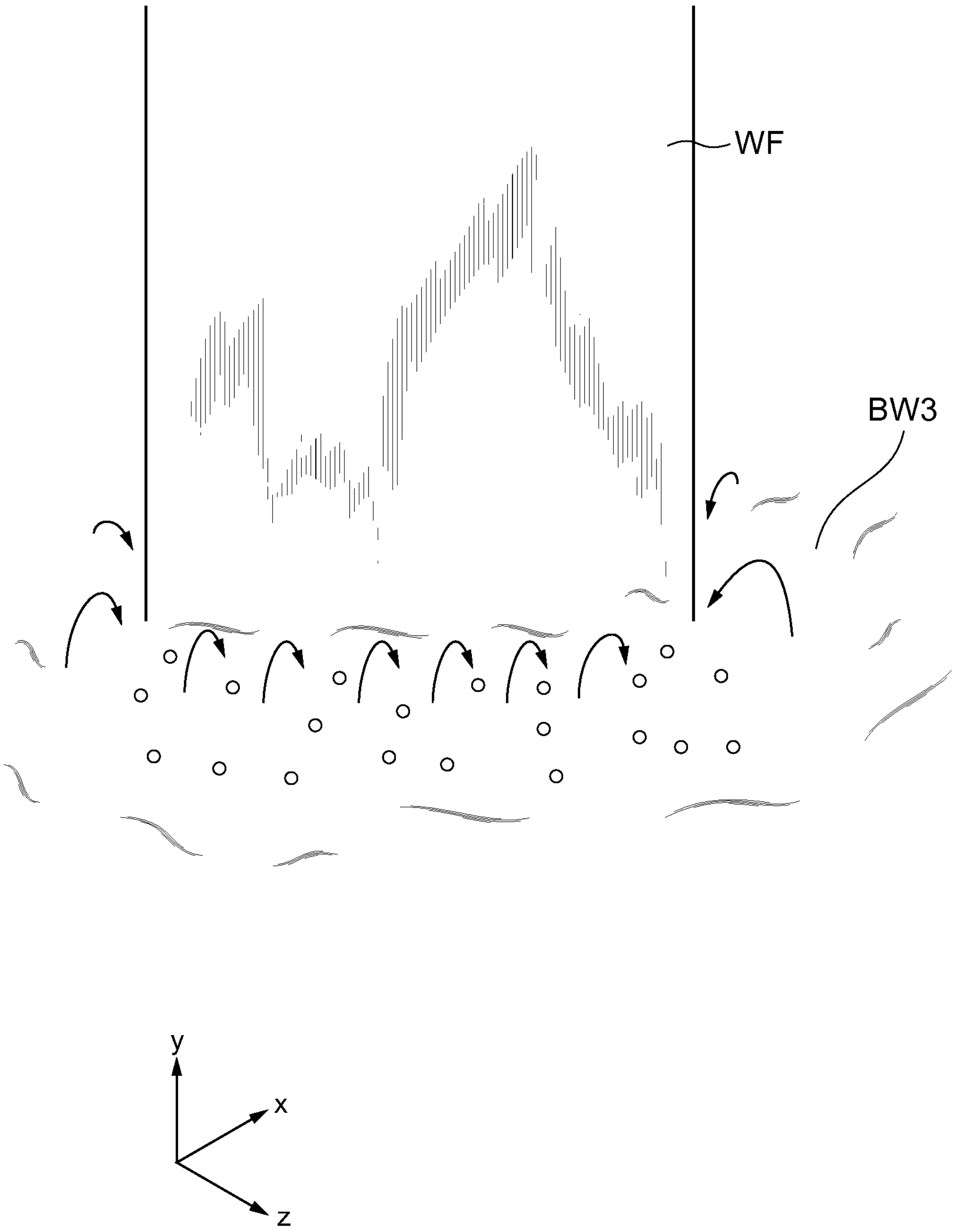
FIG. 6 is a diagram showing how bubbly water is produced in the shower apparatus according to the first embodiment of the present invention.

According to the present embodiment, the throttle channel 221 of the throttle unit 22 is formed into a flat, slit-like shape and a sheet-like stream WF is ejected through the throttle channel 221 to produce bubbly water BW containing fine bubbles. FIG. 6 schematically shows how the sheet-like stream WF plunges into the air-liquid interface BW3.

As shown in FIG. 6, a water stream ejected through the throttle channel 221 of a flat, slit-like shape rushes toward the air-liquid interface BW3 as a sheet-like stream WF having a flat cross-sectional shape. When the sheet-like stream WF plunges into the air-liquid interface BW3, in a region along the sheet-like stream WF, convection currents arranged along the direction in which the sheet-like stream WF plunges into the air-liquid interface BW3 is generated along an x direction in which the sheet-like stream WF extends in a substantially planar fashion.

When such convection currents are generated, generating directions of the convection currents coincide with each other on one side (near side of the sheet-like stream WF in FIG. 6) of the sheet-like stream WF and the rotational direction of the convection currents are opposite to the rotational direction of convection currents generated on the other side (far side of the sheet-like stream WF in FIG. 6), but the traveling directions of the convection currents coincide with each other near the air-liquid interface BW3 into which the sheet-like stream WF plunges, reducing fears that neighboring convection currents will collide with each other. On opposite ends of the sheet-like stream WF, in addition to the convection currents described above, convection currents toward the opposite ends of the sheet-like stream WF are also generated, but in regions other than the opposite ends of the sheet-like stream WF, only convection currents moving toward the sheet-like stream WF from opposite sides are generated, also reducing collisions of convection currents near the air-liquid interface BW3 when viewed as a whole.

Figure 7:
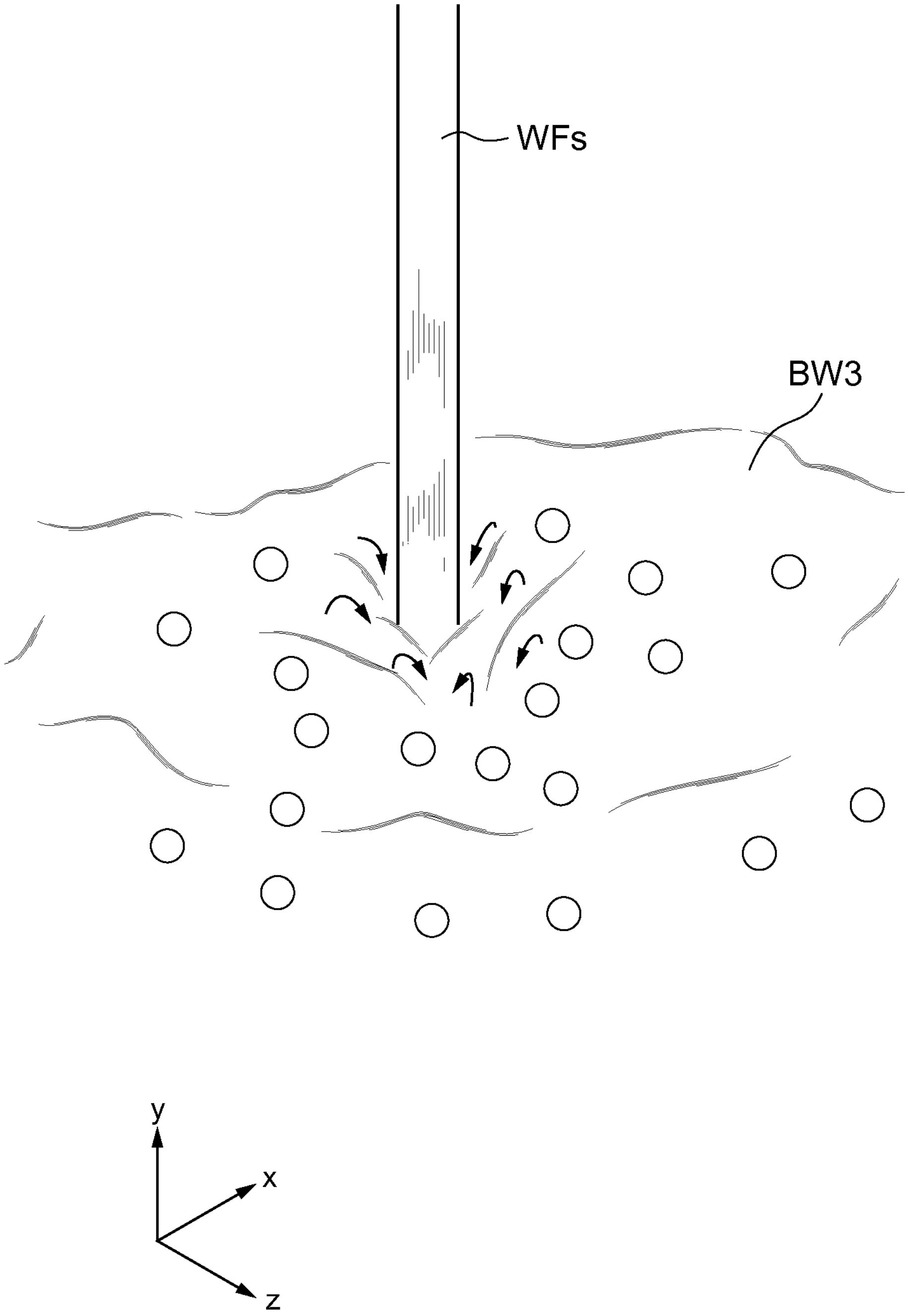
FIG. 7 is a diagram showing how bubbly water is produced in a shower apparatus according to a comparative example.

Next, a case where ejected water is caused to plunge linearly into the air-liquid interface will be described with reference to FIG. 7. FIG. 7 schematically shows how a linear stream WFs plunges into the air-liquid interface BW3.

As shown in FIG. 7, when the linear stream WFs is caused to plunge into the air-liquid interface BW3, since the water stream plunges into the air-liquid interface BW3 as a point rather than a line, convection currents are generated from all directions (all directions in an xz plane in FIG. 7) around the entry point centering on the linear stream WFs. In this way, when convection currents toward the entry point of the plunging linear stream WFs are generated from all directions around the entry point, the convection currents are put on collision course with each other. Therefore, when the linear stream WFs is caused to plunge into the air-liquid interface BW3, the convection currents generated around the entry point of the linear stream of water tend to collide with each other. This will cause collisions of air bubbles, which may result in enlargement of the air bubbles.

On the other hand, when the sheet-like stream WF is generated as in the case of the present embodiment shown in FIG. 6, convection currents which are less prone to collisions with each other are generated on both sides of an entry line along which the sheet-like stream WF plunges, as described above. Convection currents less prone to collisions with each other, when generated in this way, can reduce the possibility of air bubble enlargement due to collisions of air bubbles. If the air bubbles in the bubbly water are broken up into minute bubbles and the flow of bubbly water is made less prone to collisions, thereby maintaining the minute bubbles, even if the nozzle holes 243 are placed at locations distant from the throttle channel 221, the air bubbles are supplied to the nozzle holes 243 without being affected by buoyancy. This makes it possible to supply the bubbly water stably through all the nozzle holes 243.

As the bubbly water BW containing air bubbles of such a substantially uniform diameter is supplied to the nozzle holes 243, a bubble flow or slug flow can be formed in the nozzle holes 243 and just after discharge from the nozzle holes 243. When discharged from the nozzle holes 243, the bubbly water BW containing air bubbles of such a substantially uniform diameter and formed as a bubble flow or slug flow in this way is finely divided substantially uniformly by being sheared in a direction substantially orthogonal to a discharge direction without being turned into a mist as in the case of an annular flow. This causes water droplets of relatively large, uniform size to land continuously on the user and thereby allows the user to enjoy a shower with a voluminous feel as if the user were being showered by large drops of rain.

To achieve the operation and effect described above, the shower apparatus F1 according to the first embodiment of the present invention includes, as described above, the water supply unit 21 adapted to supply water, the throttle unit 22 installed downstream of the water supply unit 21 and adapted to make the cross sectional area of the flow channel smaller than the water supply unit 21 and thereby eject passing water downstream, the aeration unit 23 installed downstream of the throttle unit 22 and provided with the opening 231 adapted to produce bubbly water by aerating the water ejected through the throttle unit 22, and the nozzle unit 24 installed downstream of the aeration unit 23 and provided with the plurality of nozzle holes 243 adapted to discharge the bubbly water BW by being formed along the ejection direction of the water ejected through the throttle unit 22.

The throttle unit 22 includes a single throttle channel 221 which is formed into a flat shape whose longer sides run along the direction of the side wall 24*c* serving as the nozzle face in which the plurality of nozzle holes 243 are provided. The water ejected from the throttle channel 221 becomes a sheet-like stream WF, which plunges into the air-liquid interface BW3 by involving air taken in through the opening 231 and thereby producing bubbly water BW, where the air-liquid interface BW3 is an interface between air and water, the water having been temporarily pooled in the aeration unit 23 and nozzle unit 24.

Also, with the shower apparatus F1 according to the present embodiment, and the air-liquid interface BW3 is formed downstream of the opening 231, but upstream of the nozzle holes 243 (see FIG. 5).

According to the present embodiment, the water ejected from the throttle channel 221 plunges into the air-liquid interface BW3 as a sheet-like stream WF. This allows forces applied by the ejected water to be transmitted uniformly to the entire air-liquid interface BW3, making it possible to stably position the air-liquid interface BW3 between the nozzle holes 243 and opening 231. Since the air-liquid interface BW3 is formed stably and the bubbly water BW is produced by causing the sheet-like stream WF ejected from the throttle channel 221 to plunge into the air-liquid interface BW3, it is possible to induce such a flow of water that will involve surrounding air at the stable air-liquid interface as well as to increase the number of air bubbles without enlarging the air bubbles also because the convection currents around the water stream plunging into the air-liquid interface BW3 are less prone to collisions with each other.

Although in the shower apparatus F1 according to the present embodiment, the opening 231 is provided only on one side of the sheet-like stream WF, it is also preferable that at least a pair of openings 231 be provided, being placed on opposite sides of the sheet-like stream WF.

According to the present embodiment, the ejection of the sheet-like stream WF from the throttle channel 221 has the effect of inhibiting enlargement of the air bubbles as described above, but tends to restrict the movement of air across the sheet-like stream WF as well. However, if the openings 231 are provided on opposite sides of the sheet-like stream WF, air can be supplied evenly to both sides of the sheet-like stream WF, contributing to smooth production of the bubbly water BW.

In the shower apparatus F1 according to the first embodiment described above, the body 2 is shaped substantially as a rectangular parallelepiped and the water ejected from the throttle unit 22 is oriented in one direction. The scope of the present invention is not limited to the embodiment described above, and the throttle channel may be configured to radially eject the sheet-like stream of water and the plurality of nozzle holes may be arranged by being scattered in a region in which the sheet-like stream of water is ejected. The region in which the plurality of nozzle holes are placed may have any of various shapes including circular and rectangular shapes. In a second embodiment of the present invention, description will be given of an example in which the body is substantially disk-shaped and the water is ejected radially from the throttle unit.

Figure 8A:
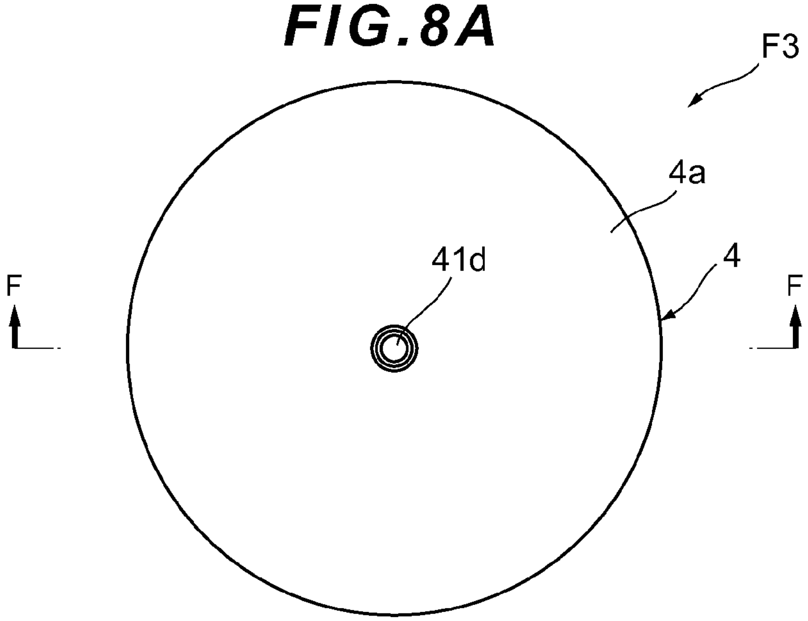
FIGS. 8(A) to 8(C) are diagrams showing a shower apparatus according to a second embodiment of the present invention, where
Figure 8B:
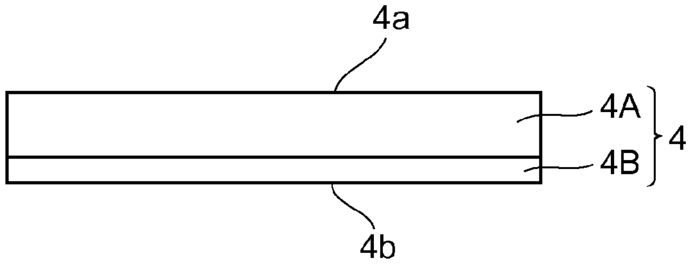
Figure 8C:
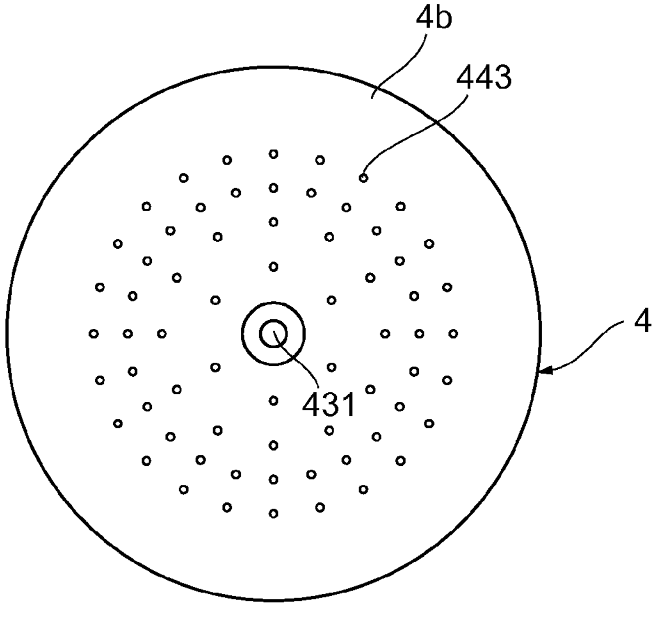

A shower apparatus which is a second embodiment of the present invention will be described with reference to FIG. 8. FIGS. 8(A) to 8(C) are diagrams showing a shower apparatus F3 according to the second embodiment of the present invention, where FIG. 8(A) is a plan view, FIG. 8(B) is a side view, and FIG. 8(C) is a bottom view. As shown in FIG. 8(A), the shower apparatus F3 mainly includes a body 4 which is substantially disk-shaped and a water supply port 41*d* is formed in a top face 4*a* of the shower apparatus F3 (body 4).

As shown in FIG. 8(B), the body 4 of the shower apparatus F3 has its external shape formed by a cavity 4A in which the water supply port 41*d* is formed and a shower plate 4B in which nozzle holes 443 are formed. As shown in FIG. 8(C), a plurality of the nozzle holes 443 and an opening 431 are formed in a bottom face 4*b* of the body 4. According to the present embodiment, the nozzle holes 443 are arranged radially around the opening 431.

Figure 9:
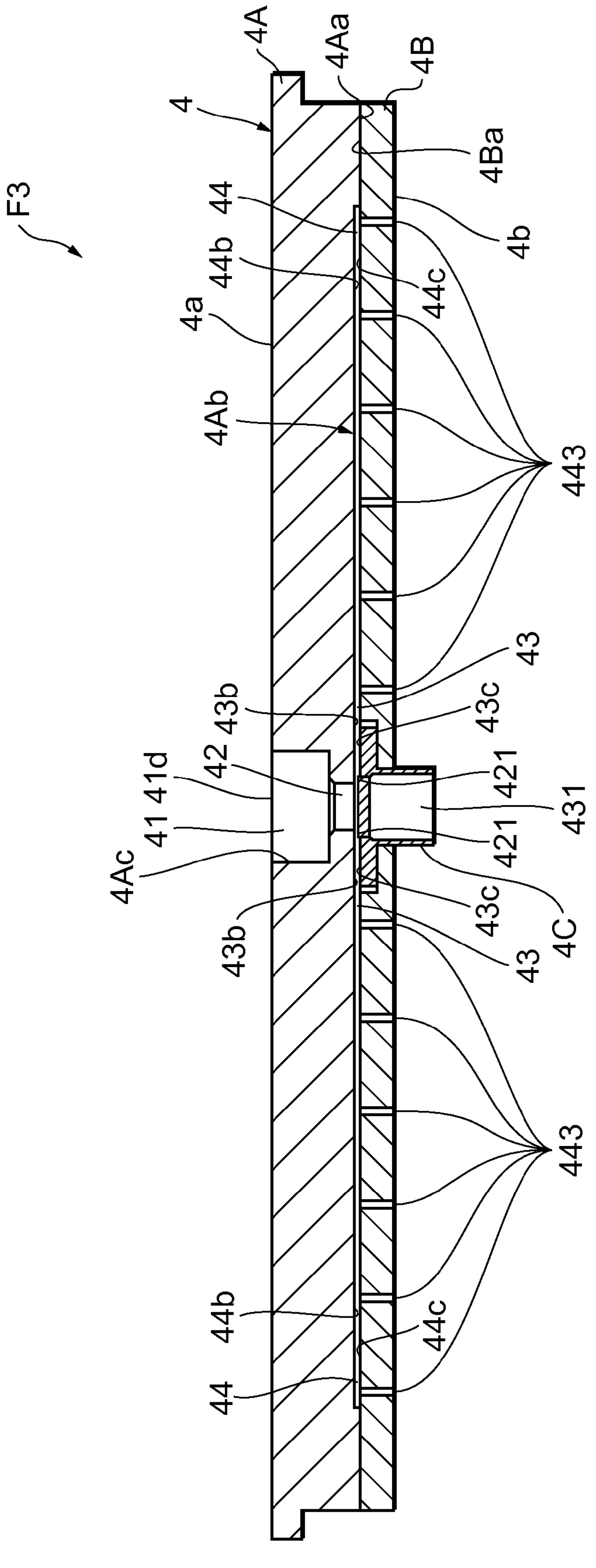
FIG. 9 is a sectional view taken along line F-F in FIG. 8(A)

Next, the shower apparatus F3 will be described with reference to FIG. 9, which is a sectional view taken along line F-F in FIG. 8(A). As shown in FIG. 9, the shower apparatus F3 includes the cavity 4A, the shower plate 4B, and a water ejection piece 4C.

The cavity 4A is a member which forms the external shape of the body 4 in conjunction with the shower plate 4B. In addition, a concave portion 4Ab circular in shape is formed extending from an abutting face 4Aa opposite the top face 4*a* of the body 4 toward the top face 4*a*.

A through-hole 4Ac is formed near the center of the cavity 4A, extending from the top face 4*a* to the concave portion 4Ab. Through the formation of the through-hole 4Ac, a water supply unit 41 is formed, extending from the water supply port 41*d* to a throttle unit 42.

The shower plate 4B is a member which forms the external shape of the body 4 in conjunction with the cavity 4A, and a plurality of the nozzle holes 443 are arranged radially in the shower plate 4B. An abutting face 4Ba opposite the bottom face 4*b* is configured to be a side wall 44*c* of a nozzle unit 44, where the bottom face 4*b* is the region in which the nozzle holes 443 are formed.

When the abutting face 4Ba of the shower plate 4B and the abutting face 4Aa of the cavity 4A are abutted against each other, a vacant space is formed between the abutting faces and the concave portion 4Ab of the cavity 4A, being configured to serve as an aeration unit 43 and nozzle unit 44. Part of the concave portion 4Ab is configured to serve as a side wall 44*a* of the nozzle unit 44.

Figure 10:
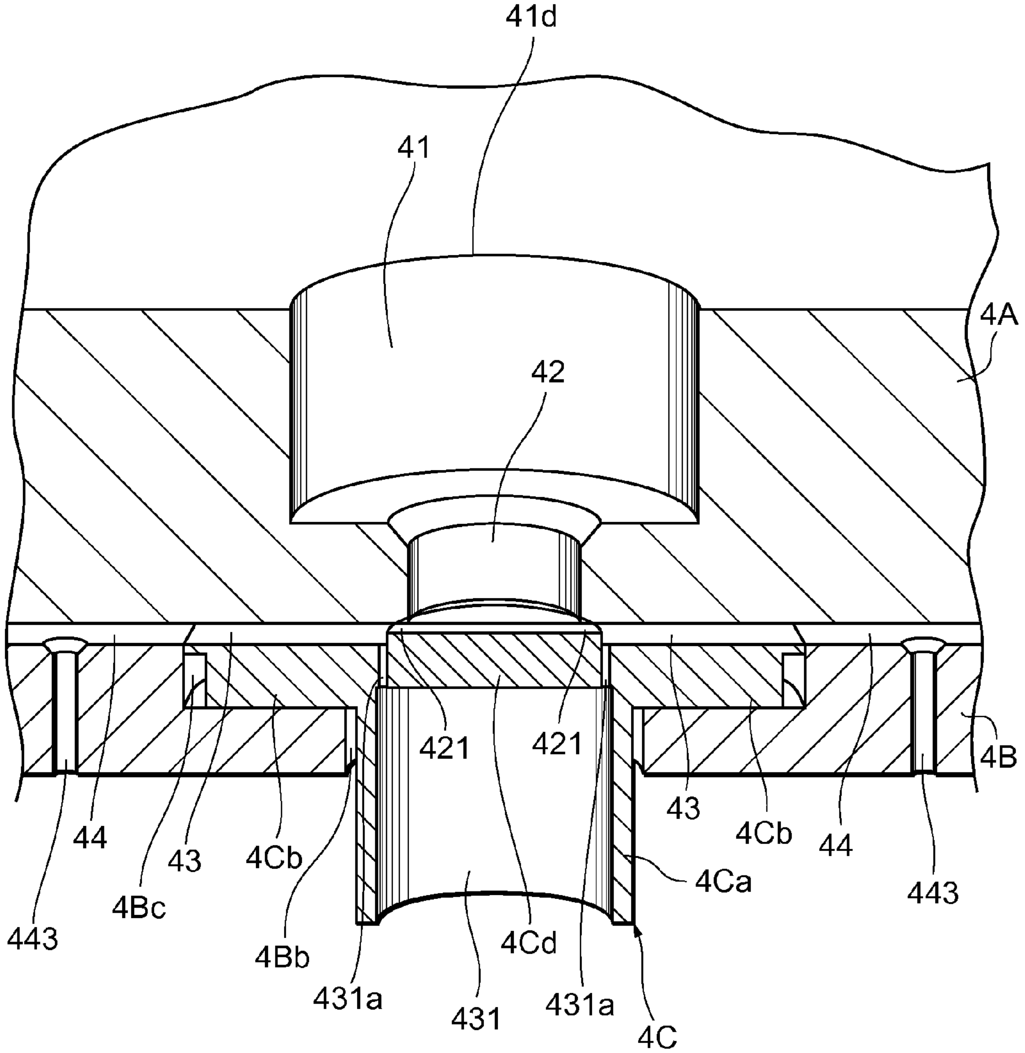
FIG. 10 is an enlarged perspective sectional view magnifying and showing a water ejection piece and its vicinity shown in FIG. 9.
Figure 11:
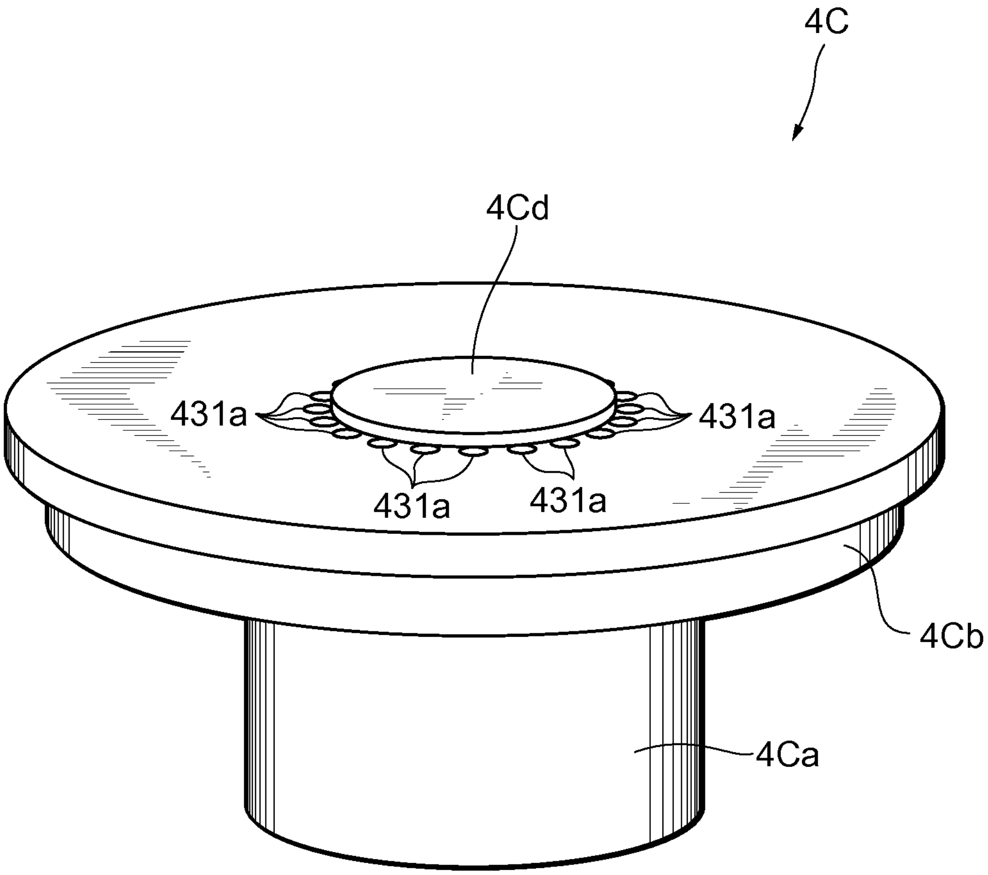
FIG. 11 is a perspective view showing the water ejection piece shown in FIG. 9.
Figure 12:
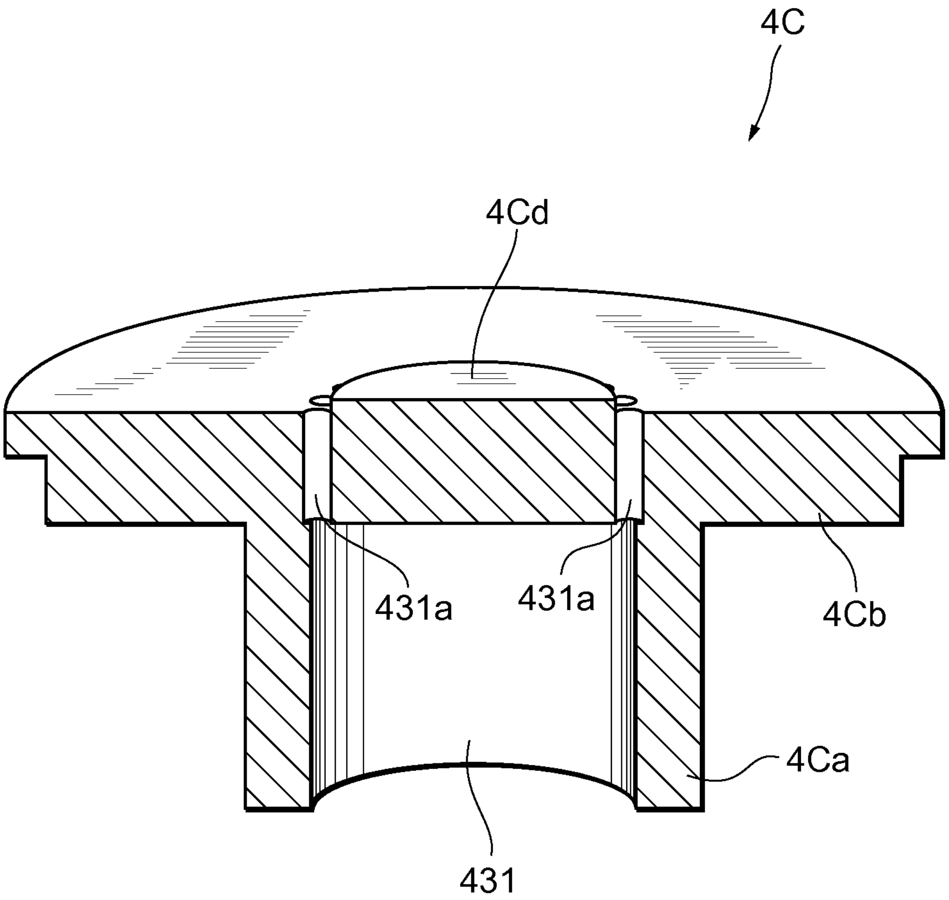
FIG. 12 is a perspective sectional view showing a cross section near the center of the water ejection piece shown in FIG. 11.

Next, the water ejection piece 4C will be described with reference to FIGS. 10 to 12. FIG. 10 is a perspective sectional view magnifying and showing the water ejection piece 4C and its vicinity. FIG. 11 is a perspective view showing the water ejection piece 4C. FIG. 12 is a perspective sectional view showing a cross section near the center of the water ejection piece shown in FIG. 11. As shown in FIGS. 10 to 12, the water ejection piece 4C, with its flange 4Cb corresponding to a brim, is shaped like a hat. Also, an air introducing projection 4Ca is formed at that end of the water ejection piece 4C which, being located opposite the flange 4Cb, corresponds to a top of the hat shape. Also, a throttle projection 4Cd is formed near the center of the flange 4Cb, i.e., on the side opposite the air introducing projection 4Ca.

The throttle projection 4Cd, which forms part of the throttle unit 42, forms a throttle channel 421 by opposing the cavity 4A. Therefore, the throttle channel 421 forms a slit all around the cavity 4A so as to eject a radial film of water from near the center of the cavity 4A.

A plurality of air introduction holes 431*a* are formed all around the throttle projection 4Cd. The air introduction holes 431*a* are intended to supply air to the throttle channel 421 and communicated with the opening 431 formed in the air introducing projection 4Ca.

In the shower plate 4B, a concave portion 4Bc circular in shape is formed, extending from the abutting face 4Ba opposite the bottom face 4*b* of the body 4 toward the bottom face 4*b*. The concave portion 4Bc is formed in the center of the shower plate 4B, being located inside the nozzle holes 443 provided radially. A through-hole 4Bb is formed in a bottom face of the concave portion 4Bc, running to the bottom face 4*b*. The water ejection piece 4C is housed in the concave portion 4Bc.

The air introducing projection 4Ca of the water ejection piece 4C is placed so as to protrude outward from the through-hole 4Bb. Therefore, the opening 431 formed in the air introducing projection 4Ca is configured to admit outside air.

When the cavity 4A, shower plate 4B, and water ejection piece 4C are assembled together as described above, the shower apparatus F3 is equipped with the water supply unit 41, throttle unit 42, an aeration unit 43, and nozzle unit 44.

The water supply unit 41 is a part intended to supply water and adapted to supply water introduced through the water supply port 41*d* to the throttle unit 42. The water supply port 41*d* can be connected with water supply means (such as a water supply hose: not shown) and the water supplied through the water supply means is supplied from the water supply unit 41 to the throttle unit 42.

The throttle unit 42 is a part installed downstream of the water supply unit 41 and adapted to make the cross sectional area of a flow channel smaller than the water supply unit 41 and thereby eject passing water downstream. A single throttle channel 421 is installed in the throttle unit 42.

The aeration unit 43 is a part installed downstream of the throttle unit 42 and provided with the opening 431 used to aerate the water ejected through the throttle unit 42 and thereby turn the water into bubbly water.

The nozzle unit 44 is a part installed downstream of the aeration unit 43 and provided with the plurality of nozzle holes 443 used to discharge bubbly water.

Figure 13:
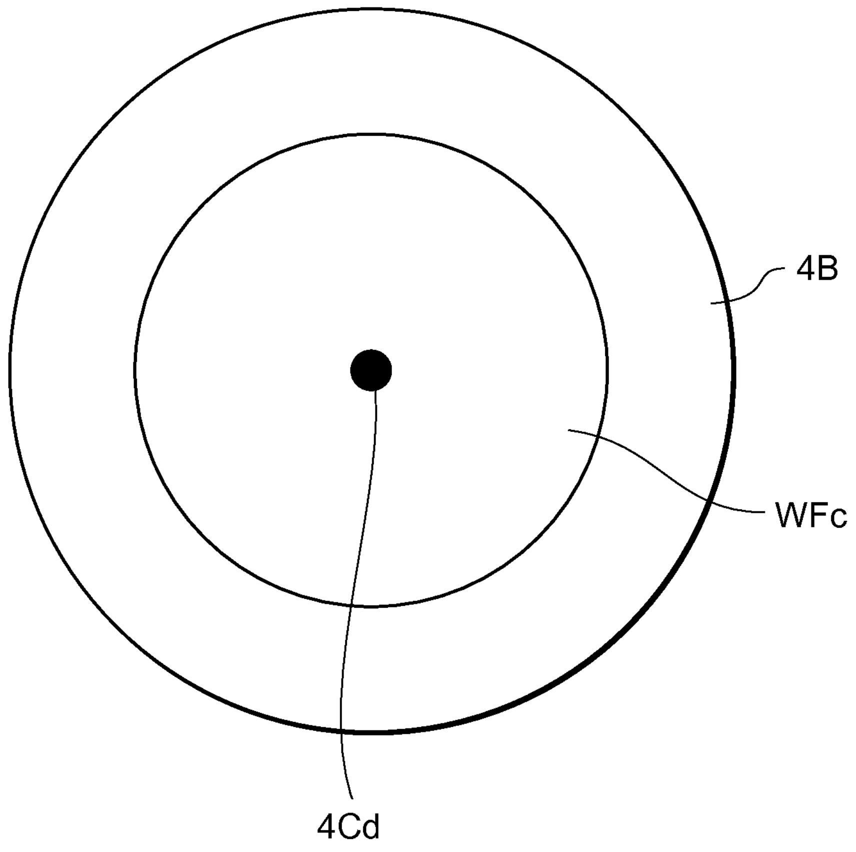
FIG. 13 is a plan view showing how water is ejected when the water ejection piece shown in FIG. 11 is used.

With the shower apparatus F3, when water is supplied from the water supply unit 41, a sheet-like stream WFc is ejected from the throttle channel 421 of the throttle unit 42. FIG. 13 shows how the sheet-like stream WFc is ejected. FIG. 13 is a diagram schematically showing how the sheet-like stream WFc is ejected when the shower apparatus F3 is viewed from the side of the water supply unit 41. As shown in FIG. 13, the sheet-like stream WFc is ejected all around.

When the sheet-like stream WFc is ejected, convection currents which are less prone to collisions with each other are generated on both sides of an entry line along which the sheet-like stream WFc plunges, as in the case of the shower apparatus F1 according to the first embodiment. Convection currents less prone to collisions with each other, when generated in this way, can reduce the possibility of air bubble enlargement due to collisions of air bubbles. If the air bubbles in the bubbly water are broken up into minute bubbles and the flow of bubbly water is made less prone to collisions, thereby maintaining the minute bubbles, even if the nozzle holes 443 are placed at locations distant from the throttle channel 421, the air bubbles are supplied to the nozzle holes 443 without being affected by buoyancy. This makes it possible to supply the bubbly water stably through all the nozzle holes 443.

As the bubbly water containing air bubbles of such a substantially uniform diameter is supplied to the nozzle holes 443, a bubble flow or slug flow can be formed in the nozzle holes 443 and just after discharge from the nozzle holes 443. When discharged from the nozzle holes 443, the bubbly water containing air bubbles of such a substantially uniform diameter and formed as a bubble flow or slug flow in this way is finely divided substantially uniformly by being sheared in a direction substantially orthogonal to a discharge direction without being turned into a mist as in the case of an annular flow. This causes water droplets of relatively large, uniform size to land continuously on the user and thereby allows the user to enjoy a shower with a voluminous feel as if the user were being showered by large drops of rain.

Figure 14:
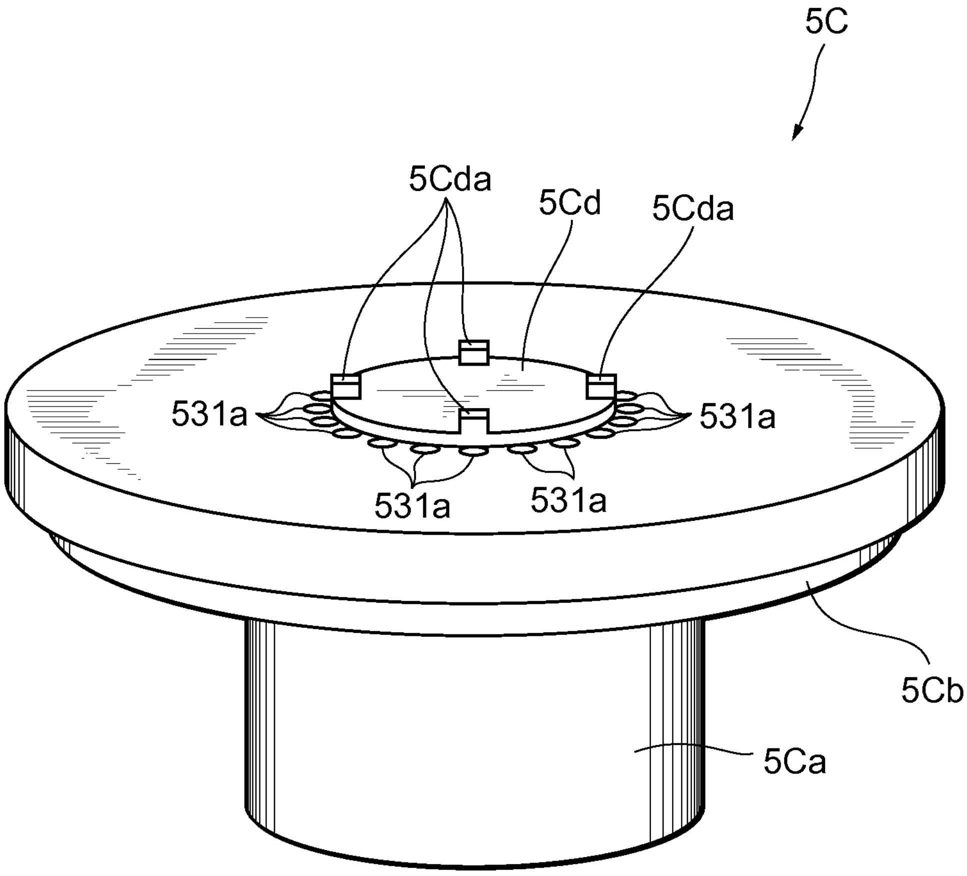
FIG. 14 is a perspective view showing a variation of the water ejection piece shown in FIG. 9.
Figure 15:
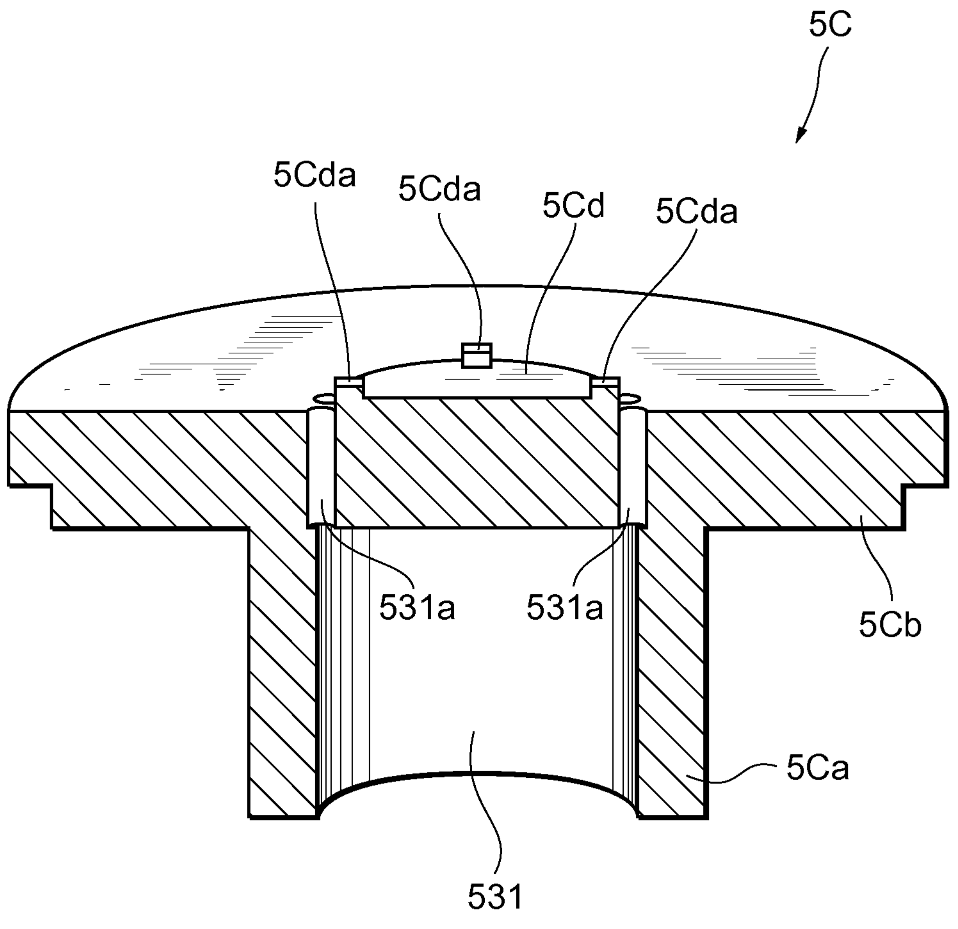
FIG. 15 is a perspective sectional view showing a cross section near the center of the water ejection piece shown in FIG. 14.
Figure 16:
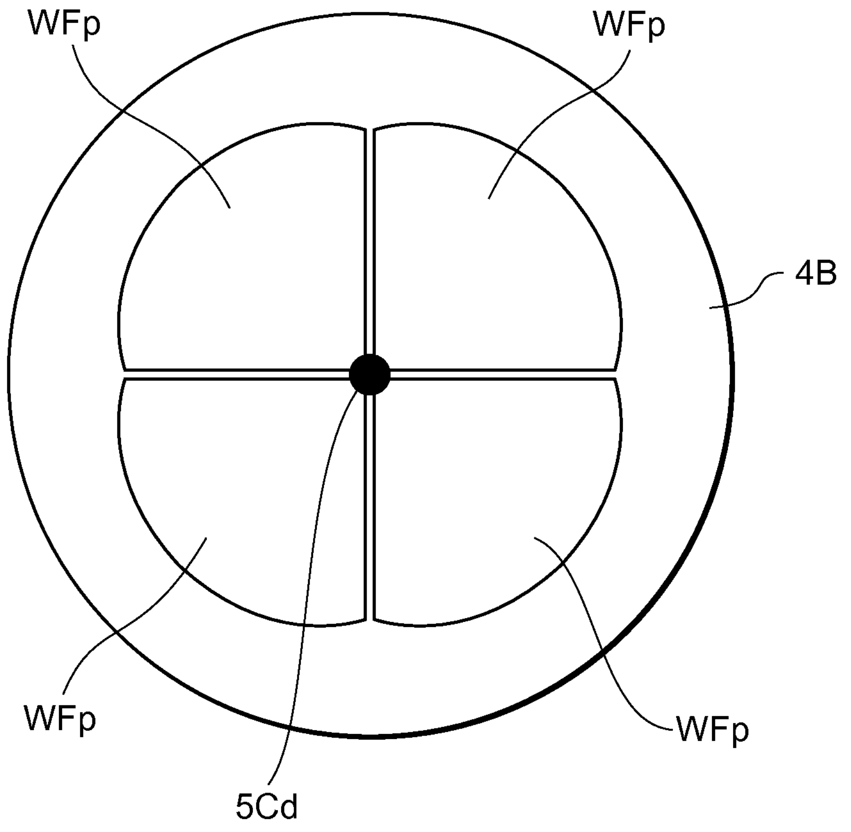
FIG. 16 is a plan view showing how water is ejected when the water ejection piece shown in FIG. 14 is used.

Although in the present embodiment, the throttle channel 421 is configured to be a single slit formed all around, it is also preferable to install a plurality of throttle channels side by side. A variation in which a plurality of throttle channels are installed side by side in this way will be described with reference to FIGS. 14 to 16. FIG. 14 is a perspective view showing a variation of the water ejection piece 5C. FIG. 15 is a perspective sectional view showing a cross section near the center of the water ejection piece 5C shown in FIG. 14. FIG. 16 is a diagram showing how a sheet-like stream is ejected when the water ejection piece 5C shown in FIGS. 14 and 15 is used instead of the water ejection piece 4C of the shower apparatus F3.

As shown in FIGS. 14 to 15, the water ejection piece 5C, with its flange 5Cb corresponding to a brim, is shaped like a hat. Also, an air introducing projection 5Ca is formed at that end of the water ejection piece 5C which, being located opposite the flange 5Cb, corresponds to a top of the hat shape. Also, a throttle projection 5Cd is formed near the center of the flange 5Cb, i.e., on the side opposite the air introducing projection 5Ca.

The throttle projection 5Cd, which forms part of the throttle unit 42, forms a throttle channel by opposing the cavity 4A. Four partition stubs 5Cda are installed on the throttle projection 5Cd. The four partition stubs 5Cda are placed by keeping a predetermined spacing from each other and adapted to play a role of partitioning the throttle channel into four parts by abutting the cavity 4A. Therefore, when the water ejection piece 5C is used, the throttle channel forms a slit divided so as to eject a radial film of water fanwise from near the center of the cavity 4A (see FIG. 16).

A plurality of air introduction holes 531*a* are formed all around the throttle projection 5Cd. The air introduction holes 531*a* are intended to supply air to the throttle channel and communicated with the opening formed in the air introducing projection 5Ca.

In this way, when the water ejection piece 5C is used, a plurality of the throttle channels are installed side by side in a direction along the nozzle face and are arranged by keeping a predetermined spacing from each other such that air can pass among sheet-like streams WFp ejected from the respective throttle channels.

According to the present embodiment, the ejection of the sheet-like stream of water from the throttle channel has the effect of inhibiting enlargement of the air bubbles as described above, but the movement of air across the water stream is restricted. However, according to the present variation, since a plurality of the flat-shaped throttle channels are installed side by side by keeping a predetermined spacing from each other, gaps are formed among the sheet-like streams WFp, allowing air to pass therethrough. Therefore, air can travel between opposite sides of the sheet-like streams WFp, and air can be supplied evenly to both sides of the sheet-like streams WFp, contributing to smooth production of the bubbly water.

In this way, according to the present variation, since air can travel between opposite sides of the sheet-like streams WFp, even if the air introduction holes 531*a* communicated with the opening is provided only on one side of the sheet-like streams, air can be supplied evenly to both sides of the sheet-like streams WFp. Thus, the simple structure in which the air introduction holes 531*a* communicated with the opening is provided only on one side of the sheet-like streams WFp can contribute to smooth production of the bubbly water.

Also, in the shower apparatus F3 according to the present embodiment, the plurality of nozzle holes 443 are arranged by being scattered in a circular region, and the throttle channels eject sheet-like streams of water radially from near the center of the circular region such that the ejected sheet-like streams WFp will be fan-shaped.

In this way, since the throttle channels are configured to eject the sheet-like streams WFp radially to the circular region in which the nozzle holes 443 are scattered from near the center of the circular region, the sheet-like streams WFp can be ejected evenly to the circular region in which the nozzle holes 443 are placed, making it possible to supply bubbly water evenly to the circular region. Also, since the sheet-like streams WFp are configured to be fan-shaped, the flow of the sheet-like streams is stabilized and bubbly water containing fine bubbles can be supplied.

An embodiment of the present invention has been described above with reference to concrete examples. However, the present invention is not limited to these concrete examples. That is, when those skilled in the art make design changes to any of the concrete examples, the resulting variations are also included in the scope of the present invention as long as the variations contain features of the present invention. For example, the components of the above-described concrete examples as well as the arrangements, materials, conditions, shapes, sizes, and the like of the components are not limited to those illustrated above, and may be changed as required. Also, the components of the above-described embodiments may be combined as long as it is technically possible, and the resulting combinations are also included in the scope of the present invention.

What is claimed is:

1. A shower apparatus for discharging aerated bubbly water, comprising:

a water supply unit adapted to supply water;

a throttle unit which, being installed downstream of the water supply unit, comprises one throttle channel formed to make a cross sectional area of a flow channel smaller than the water supply unit and thereby eject passing water downstream;

an aeration unit installed downstream of the throttle unit and provided with an opening adapted to produce the bubbly water by aerating the water ejected through the throttle unit; and a nozzle unit which, being installed downstream of the aeration unit, comprises a nozzle face having a plurality of nozzle holes adapted to discharge the bubbly water by being formed along an ejection direction of the water ejected through the throttle unit, wherein the throttle channel is formed in a wall located between the water supply unit and the aeration unit; and the water ejected from the throttle channel becomes a sheet-like stream of water which, being parallel with the nozzle face, divides the inner space of the aeration unit into two space.

2. The shower apparatus according to claim 1, wherein at least a pair of the openings are provided, being placed on opposite sides of the sheet-like stream of water.

* * * * *